United States Patent
Klein et al.

(10) Patent No.: US 11,759,189 B2
(45) Date of Patent: Sep. 19, 2023

(54) IMPLANTABLE TISSUE SCAFFOLD

(71) Applicant: LAP IQ, Los Altos, CA (US)

(72) Inventors: Michael S. Klein, Salinas, CA (US);
Michael G. Fourkas, Sunnyvale, CA (US); James Su, Newark, CA (US);
Matias Bruzoni, Redwood City, CA (US)

(73) Assignee: LAP IQ, INC., Los Altos, CA (US)

( * ) Notice: Subject to any disclaimer, the term of this patent is extended or adjusted under 35 U.S.C. 154(b) by 191 days.

(21) Appl. No.: 16/713,005

(22) Filed: Dec. 13, 2019

(65) Prior Publication Data
US 2020/0222035 A1    Jul. 16, 2020

Related U.S. Application Data

(60) Provisional application No. 62/778,634, filed on Dec. 12, 2018.

(51) Int. Cl.
*A61B 17/00* (2006.01)

(52) U.S. Cl.
CPC *A61B 17/0057* (2013.01); *A61B 2017/00004* (2013.01); *A61B 2017/00606* (2013.01); *A61B 2017/00623* (2013.01); *A61B 2017/00637* (2013.01)

(58) Field of Classification Search
CPC ...... A61B 17/0057; A61B 2017/00004; A61B 2017/00606; A61B 2017/00623; A61B 2017/00637
See application file for complete search history.

(56) References Cited

U.S. PATENT DOCUMENTS

| | | | | |
|---|---|---|---|---|
| 5,728,134 A | * | 3/1998 | Barak | A61B 17/0057 128/899 |
| 6,171,329 B1 | * | 1/2001 | Shaw | A61B 17/0057 606/151 |
| 6,726,696 B1 | * | 4/2004 | Houser | A61B 17/0057 606/151 |
| 8,992,567 B1 | * | 3/2015 | Houser | A61B 17/0057 606/213 |
| 2001/0037129 A1 | * | 11/2001 | Thill | A61B 17/0057 606/213 |
| 2002/0010481 A1 | * | 1/2002 | Jayaraman | A61B 17/0057 606/151 |

(Continued)

*Primary Examiner* — Alexander J Orkin
(74) *Attorney, Agent, or Firm* — Edell, Shapiro & Finnan, LLC

(57) ABSTRACT

A biodegradable scaffold for wound closure including a central rod and two spaced-apart plates. The central rod may have an engagement block on top for stabilizing an implanting tool. The two spaced-apart plates include an upper plate connected to the central rod and a lower plate connected to the central rod. Each of the upper and lower plates may include perforations which may be useful for detachably connecting an implanting tool and which encourage ingrowth of the tissue. The biodegradable scaffold allows tension free anatomic alignment of tissue within the plates and facilitates wound healing. The upper and lower plate may have a helical portion, in which each plate may extend around the central rod. The helical portion serves to draw or pull tissue around the wound defect into the scaffold in the course of deploying the scaffold.

19 Claims, 8 Drawing Sheets

(56) References Cited

U.S. PATENT DOCUMENTS

| | | | | |
|---|---|---|---|---|
| 2004/0215231 A1* | 10/2004 | Fortune | ............... | A61B 17/686 606/213 |
| 2005/0043759 A1* | 2/2005 | Chanduszko | ...... | A61B 17/0057 606/213 |
| 2005/0182495 A1* | 8/2005 | Perrone | ............. | A61B 17/0057 623/23.72 |
| 2005/0251154 A1* | 11/2005 | Chanduszko | ...... | A61B 17/0057 606/151 |
| 2006/0052821 A1* | 3/2006 | Abbott | .................. | A61B 17/064 606/213 |
| 2010/0016887 A1* | 1/2010 | Inderbitzi | .......... | A61B 17/0057 606/213 |
| 2010/0087854 A1* | 4/2010 | Stopek | ................... | A61L 27/58 606/215 |
| 2011/0040324 A1* | 2/2011 | McCarthy | .......... | A61B 17/3421 606/215 |
| 2011/0184439 A1* | 7/2011 | Anderson | .......... | A61B 17/0057 606/151 |
| 2012/0071918 A1* | 3/2012 | Amin | ................ | A61B 17/0057 606/213 |
| 2013/0338778 A1* | 12/2013 | Drori | ...................... | A61F 2/442 623/17.16 |
| 2014/0155934 A1* | 6/2014 | Baxter | ............... | A61B 17/0057 606/215 |
| 2014/0371788 A1* | 12/2014 | Wang | ................ | A61B 17/0057 606/215 |
| 2017/0156904 A1* | 6/2017 | Liu | ........................... | A61F 2/86 |

* cited by examiner

IMPLANTABLE TISSUE SCAFFOLD

RELATED APPLICATION

This Application claims priority from U.S. Provisional Patent Application 62/778,634, entitled Implantable Tissue Scaffold, filed Dec. 12, 2018.

FEDERAL GRANTS

This invention was made with government support under SBIR Grant Number 1R43HD086896-01A1 NICHD awarded by the Small Business Administration. The government may have certain rights to the invention.

BACKGROUND

Technical Field

The present invention generally relates to a wound closure device and more specifically to a wound closure device to repair a defect left during laparoscopic (minimally invasive) surgery.

Laparoscopic surgery was introduced as an alternative to open surgical methods. Also referred to as minimally invasive surgery, the technique allows for small incision access to the intra-abdominal cavity, or other internal body cavities. The approach utilizes specialized equipment such as robotics for the purposes of inflating the abdominal cavity with gas, deploying and exchanging instruments during the operation, and real time imaging with a videoscopic camera.

A laparoscopic trocar is a surgical device used for laparoscopic procedures to pierce and access the wall of an anatomical cavity, thereby forming a passageway providing communication with the inside of the cavity. Other medical instruments such as videoscopes and operating instruments can thereafter be inserted through the passageway to perform various medical procedures within the anatomical cavity. The general background is also discussed in U.S. Pat. No. 9,615,817 to Bippart et al. which is hereby incorporated by reference for all purposes herein.

When the procedures are over, the laparoscopic trocar is removed, leaving a residual defect in the fascia-peritoneal layer. Laparoscopic trocars are typically 5-15 mm in diameter. The risk of herniation increases as the trocar size increases, and it is generally recommended that any port size larger than 5 mm should be closed because of the risk of hernias. The residual fascia peritoneal layer defect is located deep in the abdominal wall, making it difficult to view and for the surgeon to repair.

Trocar site herniation is a recognized complication of laparoscopic surgery. Omental, and sometimes intestinal, herniation with incarceration and obstruction has been documented in recent surgical literature, occurring at any trocar insertion site larger than 5 mm that was not properly sutured at operation. The necessity to perform fascial closure of any trocar insertion site larger than 5 mm has now been established and is routinely practiced worldwide.

However, the closure of such a trocar site fascial defect using the conventional suturing technique is often technically difficult, frustrating, unreliably successful, and even sometimes dangerous due to the limited size of skin incision, the thickness of the subcutaneous fatty layer, and necessity of blind manipulation. Moreover, the suturing that involves placement of deep blind sutures after the abdomen has been decompressed is a dangerous manipulation that surgeons prefer to avoid.

A number of techniques and instruments have been proposed to facilitate a safe and secure closure of the fascial defect through the tiny skin opening. Many of these repairs include passing in any way a suture from one side of the trocar wound to the other, and its ligation. For this purpose either a curved needle or a variety of straight needles through which sutures are passed have been used. Problems arise as both sides of the defect may not be sutured. Also, in overweight and obese patients with thick abdominal walls, reliable fascia closure is very difficult to achieve. This results in a delayed hernia formation such as an incarcerated or symptomatic hernia. The literature shows as much as a 6% overall hernia complication rate, resulting in reoperation, rehospitalization, and extended disability. In the worst case this results in the need for an emergent repair, resulting in rehospitalization.

Suturing techniques require positioning of the camera and grasping, visualization of the needles during their entrance into the peritoneal cavity, feeding of the graspers or suture passers with the suture loop, all of which are repeated once or twice for every trocar defect closed. Any of these suturing techniques are not only time and effort consuming, even in the best of hands. As more defects at various sites in the abdominal wall are to be closed after advanced laparoscopic operations, the suturing techniques have become more complicated and tedious.

Techniques using instruments such as suture passers work by adding a catch onto the end of a needle assembly. These guide positioning of the suture fixed point beyond the edges of the trocar defect and assure primary closure when direct visualization is limited from the outside. Intracorporeal laparoscopic closure techniques employ suture passers with a modified clasp or spacers at the end of the needle assembly. These guide positioning of the suture at a fixed point beyond the edge of the trocar defect and assure primary closure when direct visualization is limited from the outside and conventional suturing is not possible.

Moreover, a series of manipulations is needed to complete a single suturing. The conventional suturing technique involves much traumatic manipulation including pushing, pulling and retraction of the wound, and insertion and extraction of needles. Most of the time the needle is passed twice, and sometimes more. As manipulation in the wound increases, the inflammation and risk of ensuing infection rise considerably. The edema and the collection of seroma and hematoma at the wound further cause dehiscence and hernia formation on a long-term basis.

Excessive traumatic manipulation and suturing with heavy sutures oppose the "minimally invasive" basis of laparoscopic surgery. The patients are subject to pain and complications at their trocar sites in the postoperative period.

Tedious intra-corporeal suturing techniques can be used to dose trocar port defects under direct vision from within the abdominal cavity, but this is rarely done. Instead, most trocar ports are dosed from the outside, with the abdominal wall in a flattened configuration.

As a result, the residual defect within the fascial layer is poorly visualized by the surgeon. No matter which suturing technique or needle is used, it is not possible to eliminate the trocar site hernias completely. As described in Malazgirt (US Patent Application, pub #20060015142 published Jan. 19, 2006), the current incidence is reportedly between 0.77-3%.

As complex laparoscopic surgery has become more common, the incidence of this complication has also increased.

The reported rates of hernia show that there is not yet any superior method in the safe closure of the trocar fascial defect.

U.S. Pat. No. 6,120,539 issued Sep. 19, 2000 proposed a prosthetic repair fabric constructed from a combination of non-absorbable tissue-infiltratable fabric which faces the anterior surface of the fascia and an adhesion-resistant barrier which faces outward from the fascia. This prosthetic requires the use of sutures to hold it in place.

U.S. Pat. No. 5,366,460, issued Nov. 22, 1994 proposed the use of a non-biodegradable fabric-coated loop inserted through the defect into the fascia wall, pressing against the posterior fascia wall from the intra-abdominal pressure.

U.S. Pat. No. 6,241,768, issued Jun. 5, 2001 proposed a prosthetic device made of a biocompatible non-biodegradable mesh, which sits across the fascia defect using the abdominal pressure to hold it in place.

US Published Patent Application 2003/0181988 proposed a plug made of biocompatible non-biodegradable material which covers the anterior side of the fascia, the defect, as well as the posterior side of the fascia.

US Published Patent Application 2006/0015142 proposed a plug/mesh non-biodegradable combination for repair of large trocar wounds. It is stated that it requires at least a "clean flat area around with a radius of 2.5 cm", and requires staples to hold it in place.

Ford and Torres (Pat Pub #20060282105) proposed a patch with a tether or strap, all made of non-biodegradable biocompatible material placed against the anterior wall of the fascia defect.

All of the above references are hereby incorporated by reference as if fully set out herein.

SUMMARY

One embodiment of the invention is an implantable tissue scaffold for wound closure which includes a central rod, an upper plate angularly positioned on the central rod; and a lower plate that is also angularly positioned on central rod. The spacing on the central rod of the upper and lower plate is determined by the thickness of the defect caused by the laproscopic tocar, and may vary. This allows the tissue scaffold to be positioned such that one plate is on a tissue surface on one side of the tunnel like defect, and the other plate is on the other side of the tunnel like tocar defect. One unique feature of the implantable tissue scaffold is that it is a single, unitary piece. This allows the tissue scaffold to be adaptable to 3-D printing, and simpler to manufacture as it has no moving parts. Another unique feature is that it is made of a biodegradable material, which will biodegrade once placed within 3-5 months.

The tissue scaffold may have a number of configurations. For example, the upper and lower plates may be in part essentially perpendicular to the central rod. The upper and lower plates may be divided into fractional sections, such as quadrants, which are circumferentially positioned about the central rod. One or more of the upper and lower plate may camber helically. Such a shape aids the implantable tissue scaffold in seating on either side of the trocar defect. The surface of the plates may include features to both promote tissue growth through the tissue scaffold and to aid in gripping the device by an implanting or placement tool. For example, the upper and lower plates may include perforations, such as an inner and outer row of perforations through the upper and lower plates. These perforations promote through growth and allow a tool, such as a gripping tool, to position/implant the implantable tissue scaffold.

Such perforations on the upper and lower plates may be in multiple rows. These perforations reduce the material required to manufacture the device, provides a feature to grip onto the device by a tool, and promotes tissue ingrowth.

DETAILED DESCRIPTION

Figure 1:
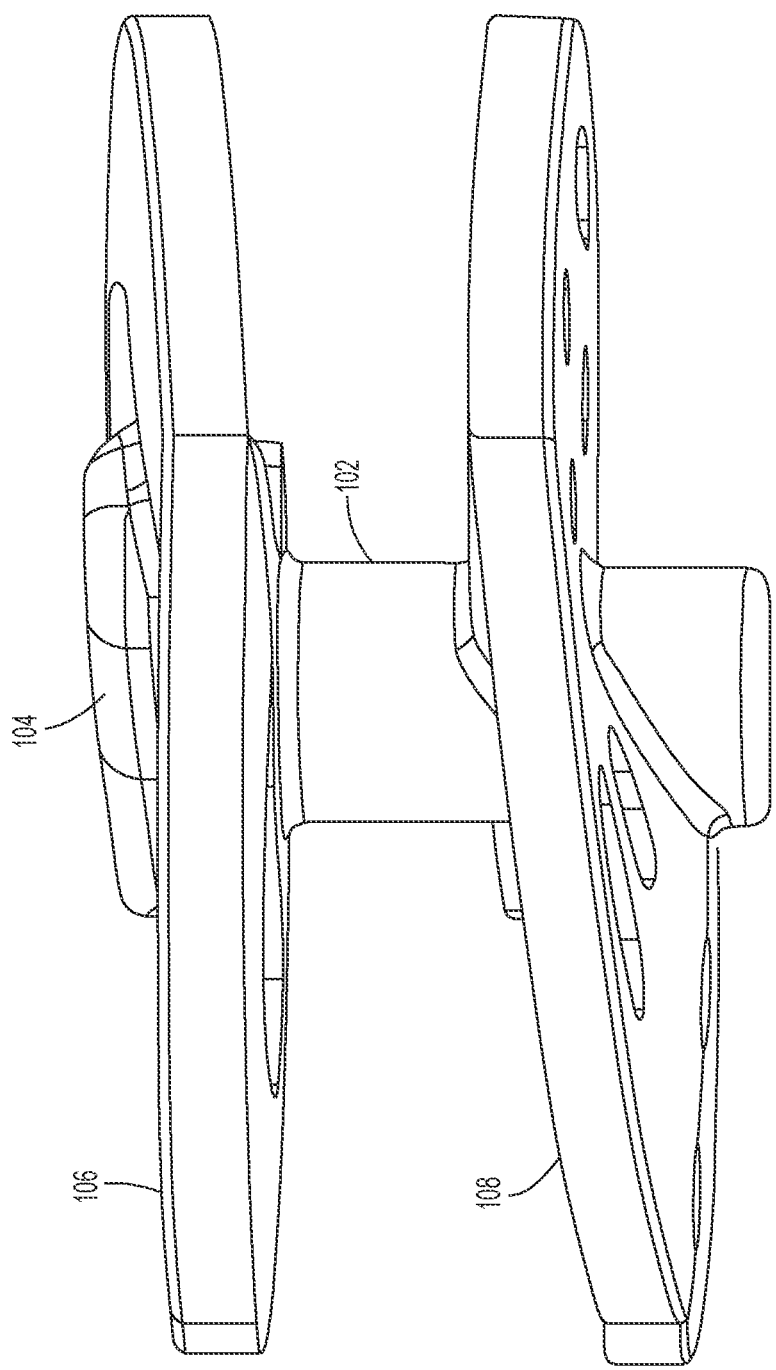
FIG. 1 shows a first side view of an embodiment of the invention.

Specific embodiments and examples are illustrated in the figures and described in the detailed description. However, it is envisioned that the disclosed tissue scaffold may be put into practice using any of a number of elements, and could be made using a variety of methods, whether presently known or not. The present disclosure should in no way be limited to the exemplary implementations and techniques illustrated in the drawings and described below. In addition, elements, features and designs illustrated in the drawings are not necessarily drawn to scale.

In one or more embodiments, as shown in FIG. 1, the device includes a central rod 102, an engagement block attached to the one end of the central rod 104, an upper plate 106, and a lower plate 108 essentially perpendicular to the central rod 102. The plates are at least in part essentially parallel to each other with enough space between to allow the tissue to seat without direct compression. This spacing is designed for the average tissue thickness at common sites of trocar insertion. In initial tests it has been found that even when the implantable tissue scaffold is too small to seat at the outer and inner peripheral edges of a trocar defect, the device still has clinical benefit. For example, in obese patients, the tissue thickness may be variable, and the trocar insertion may leave a larger defect. In such instances it has been found that the implantable tissue scaffold may position within a passageway of the defect and results in tissue ingrowth prior to device biodegradation.

In one embodiment, the upper and lower plates are designed in a screw-like manner, such that opposing ends of the upper plate 106 are attached to the engagement block 104 on the central rod 102, and that the upper end of the upper plate 106 aligns with the top side of the engagement block 104, and the lower end of the upper plate 106 aligns with the bottom side of the engagement block 104. In this embodiment, the base element of each plate is a three-quarter circle where the first and second quadrants are essentially perpendicular to the engagement block 104, and the third quadrant cambers helically. The corner of the first quadrant is rounded to avoid any sharp edges, while the edge of the third quadrant has a semi-circular attachment which attaches on one side to the outside of the inner edge and on the inside to where the edge meets the central rod 102. The quadrant that is helical on the upper plate 106 is the opposite of the quadrant of the lower plate 108 supporting defect edges of tissue alignment where the scaffold is encouraged to stay near the wound without injuring the tissue.

The term scaffold as used here is to define the surfaces of the upper plate and lower plate which contact and align the tissue, into which the tissue will grow as the plates disintegrate. In one embodiment, the upper and lower plates have perforations which aid in this process.

In other embodiments, the first and third quadrants of each of the upper plate 106 and lower plate 108 are perpendicular to the central rod 102, while the middle quadrant is helical in the same direction. However instead of a single 90-degree arc, the third quadrant provides a complete loop as well, about 5 quadrants or 450 degrees, which provides more of a grabbing effect on the tissue between the two plates, further encouraging the scaffold to stay aligned with the wound. The term quadrants are illustrative of a division of the plates into fractional sections. The plates are circumferential about the central rod 102. These plates may be something less than 360 degrees about the central rod, make a single 360 degree covering, or include 5 quadrants and be about 450 degrees to magnify the grabbing effect of the device.

Figure 2:
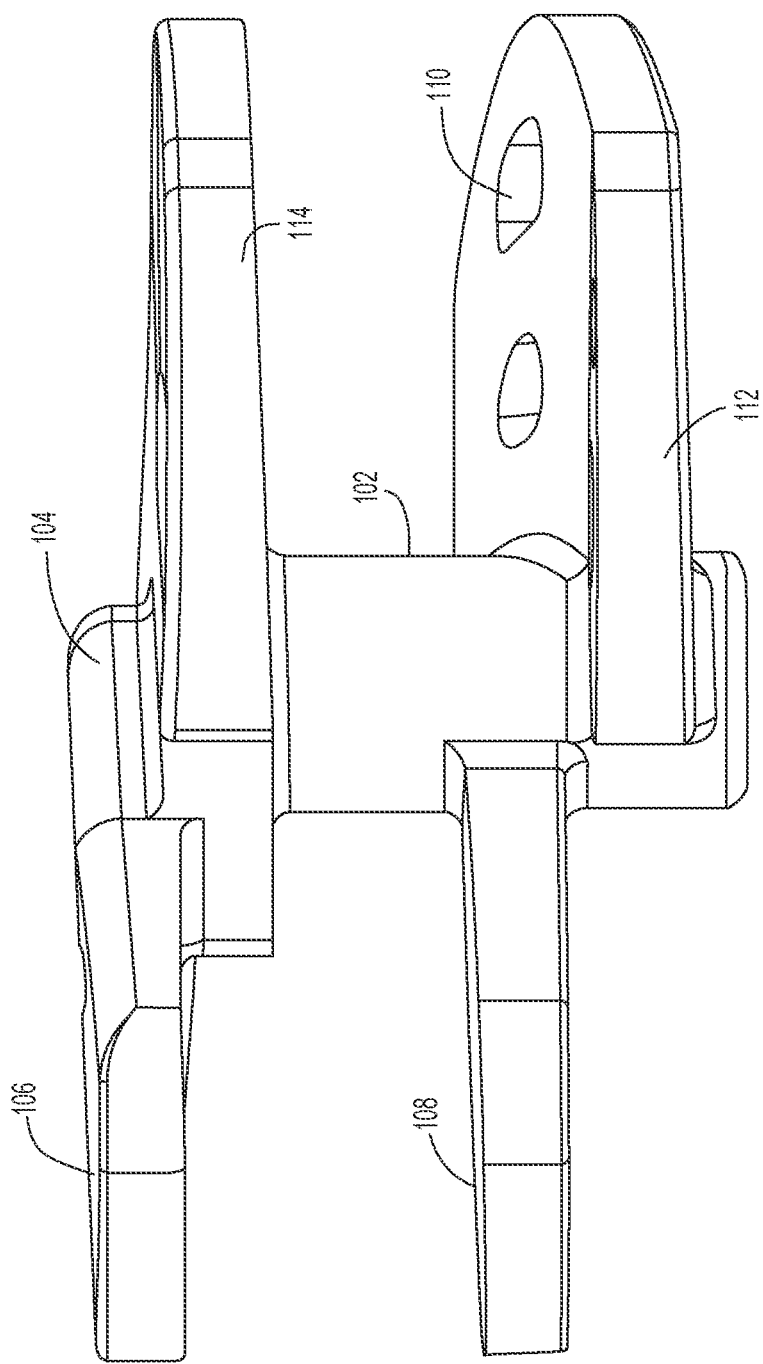
FIG. 2 shows a second side view of an embodiment of the invention.

FIG. 2 shows a side view of the device showing the lower end 112 of the lower plate 108 and the lower end 114 of the upper plate 106. This view shows the lower base perforations 110 which are present on the lower plate. In one or more embodiments, there are one or more perforations present in each quadrant of the plate. The lower base perforations 110 both encourage growth into the scaffold and reduce the weight of the device. In addition, the perforations could be a feature to allow a tool to grip onto the implantable tissue scaffold and position the device. Although upper plate 106 and lower plate 108 are shown having essentially flat surfaces, it is contemplated that textured surfaces could be used to aid in the stable positioning of the device. In this illustrated embodiment, the perforations are elliptical, however any variety of shapes are possible. These perforations shown pass through the entire plate and are uniform in diameter. It is also contemplated that the pore shapes could taper, be more circular or angular or have other shapes or designs. The illustration shows the perforations in both the lower and upper plates with one set of perforations disposed closer to the central rod.

Figure 3:
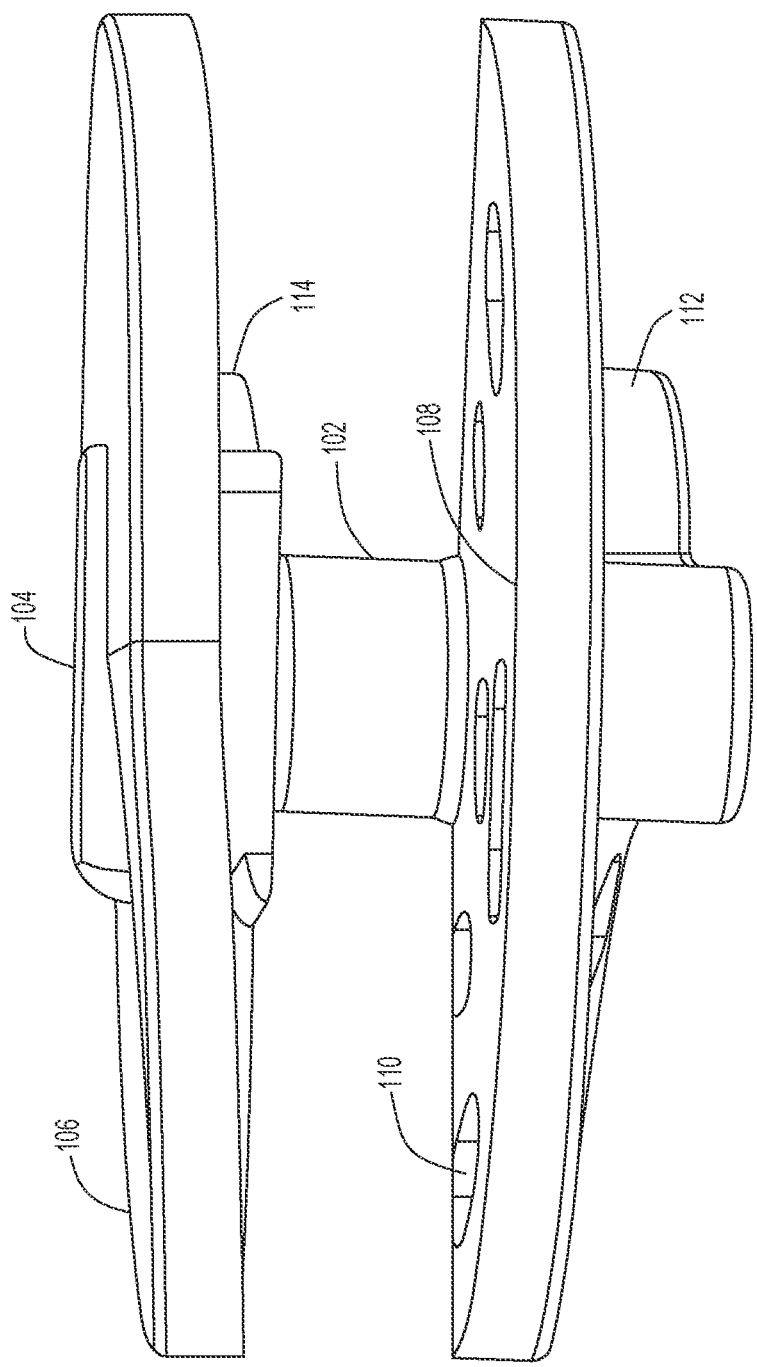
FIG. 3 shows a third side view of an embodiment of the invention, FIGS. 1-3 showing various views about the circumference of an embodiment of the invention.

FIG. 3 shows a side view of an embodiment looking at a different side view of the device, such that the lower end 114 of the upper plate 106 and the lower end 112 of the lower plate 108 are on the opposite side of that shown in FIG. 2.

Figure 4:
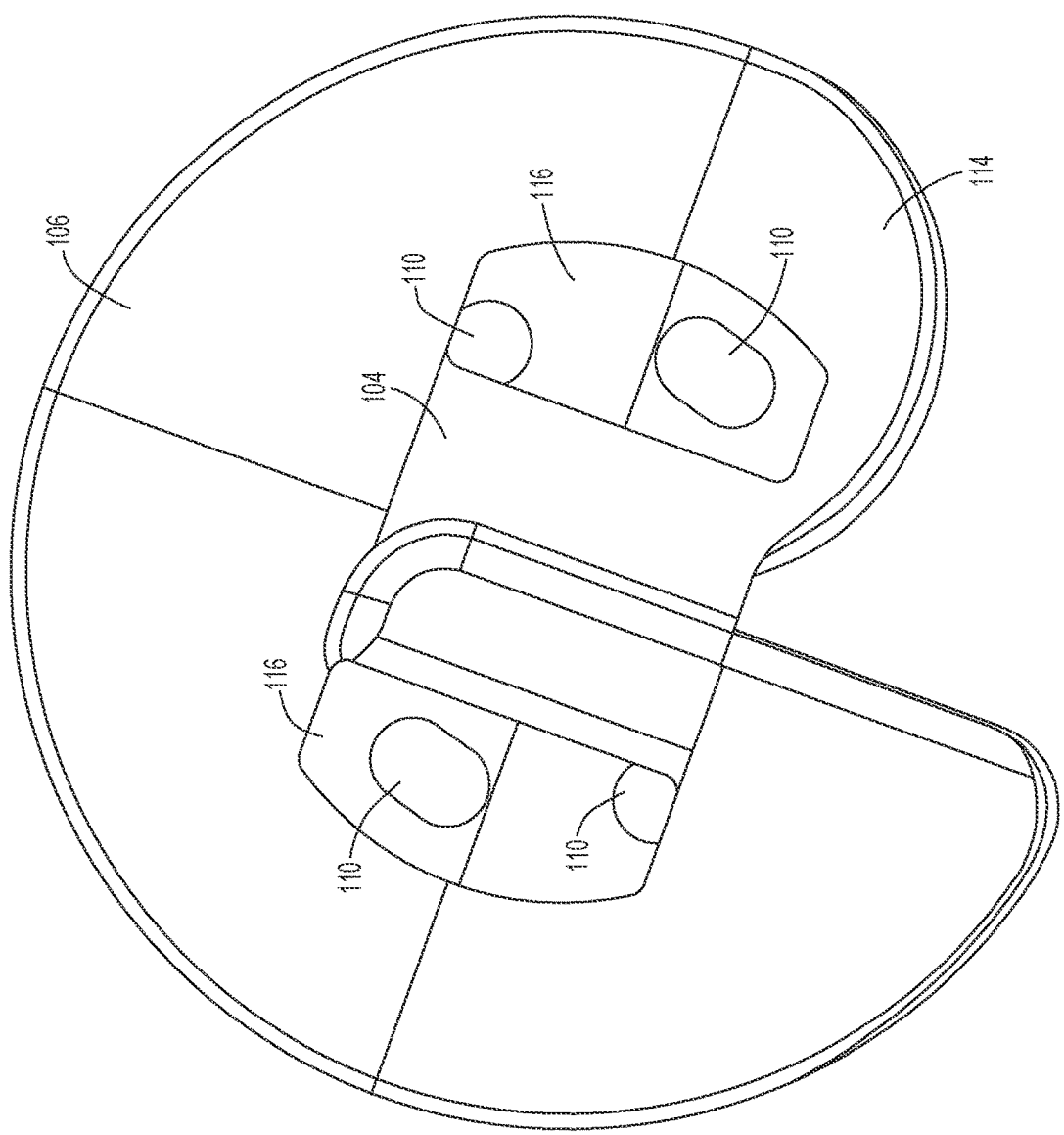
FIG. 4 shows a top view an embodiment of the invention.

FIG. 4 shows a top view of an embodiment of FIGS. 1-3, showing the engagement block 104 connected to the upper plate 106, the lower end of the upper plate 114 and the upper plate perforations 110. The upper plate perforations 110 serve both to encourage growth as well as to provide a place for the instrument placing the device into the wound to hold and stabilize it. As shown, upper plate perforations 110 are larger than the perforations of lower plate 108, and instead of an elliptical shape has a flat surface closest to the central rod 102, two essentially perpendicular side walls and a curved outer wall at the radial greater distance from central rod 102. These larger perforations with flat surfaces are more suited to grasping by a positioning tool during implantation of the implantable tissue scaffold.

Figure 5:
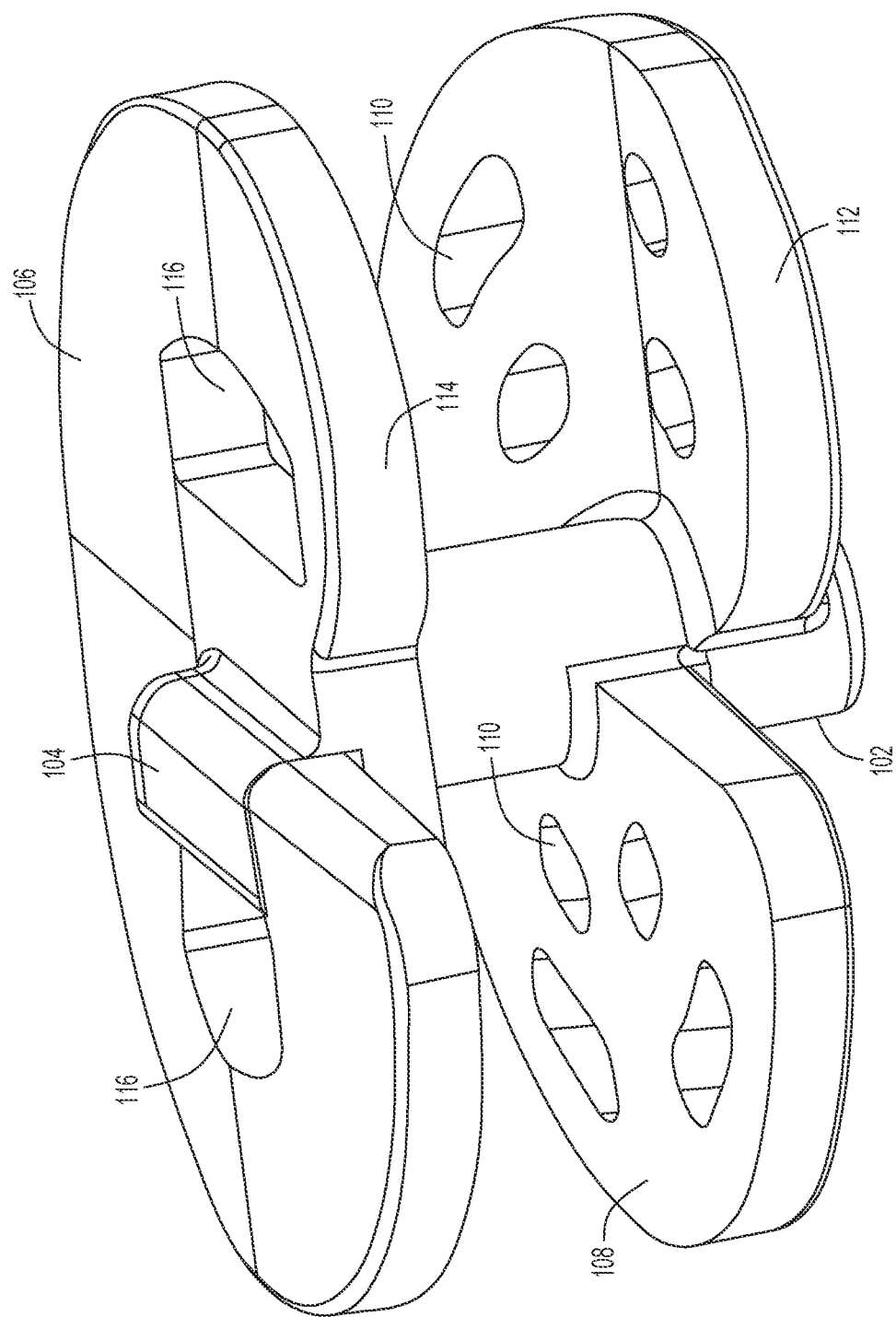
FIG. 5 shows a side perspective view of an embodiment of the invention showing the upper sides of the upper and lower plates.

FIG. 5 shows a side perspective view of an embodiment, looking down at the top of the device at an approximate 45-degree angle.

Figure 6:
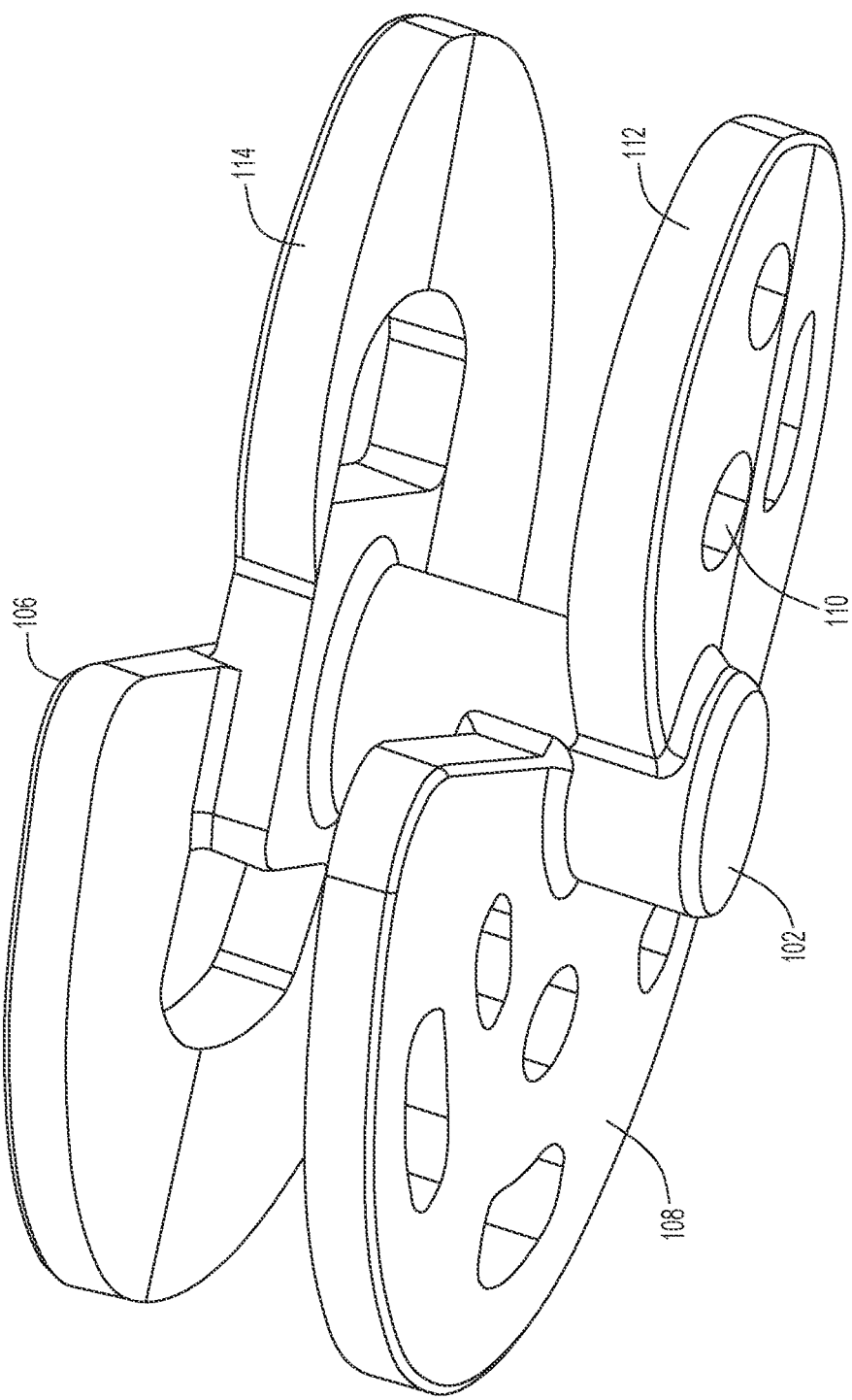
FIG. 6 shows a side perspective view of an embodiment of the invention showing the lower sides of the upper and lower plates.

FIG. 6 shows an upward view of an embodiment, looking up at the bottom of the device a tan approximate 45-degree angle.

Figure 7:
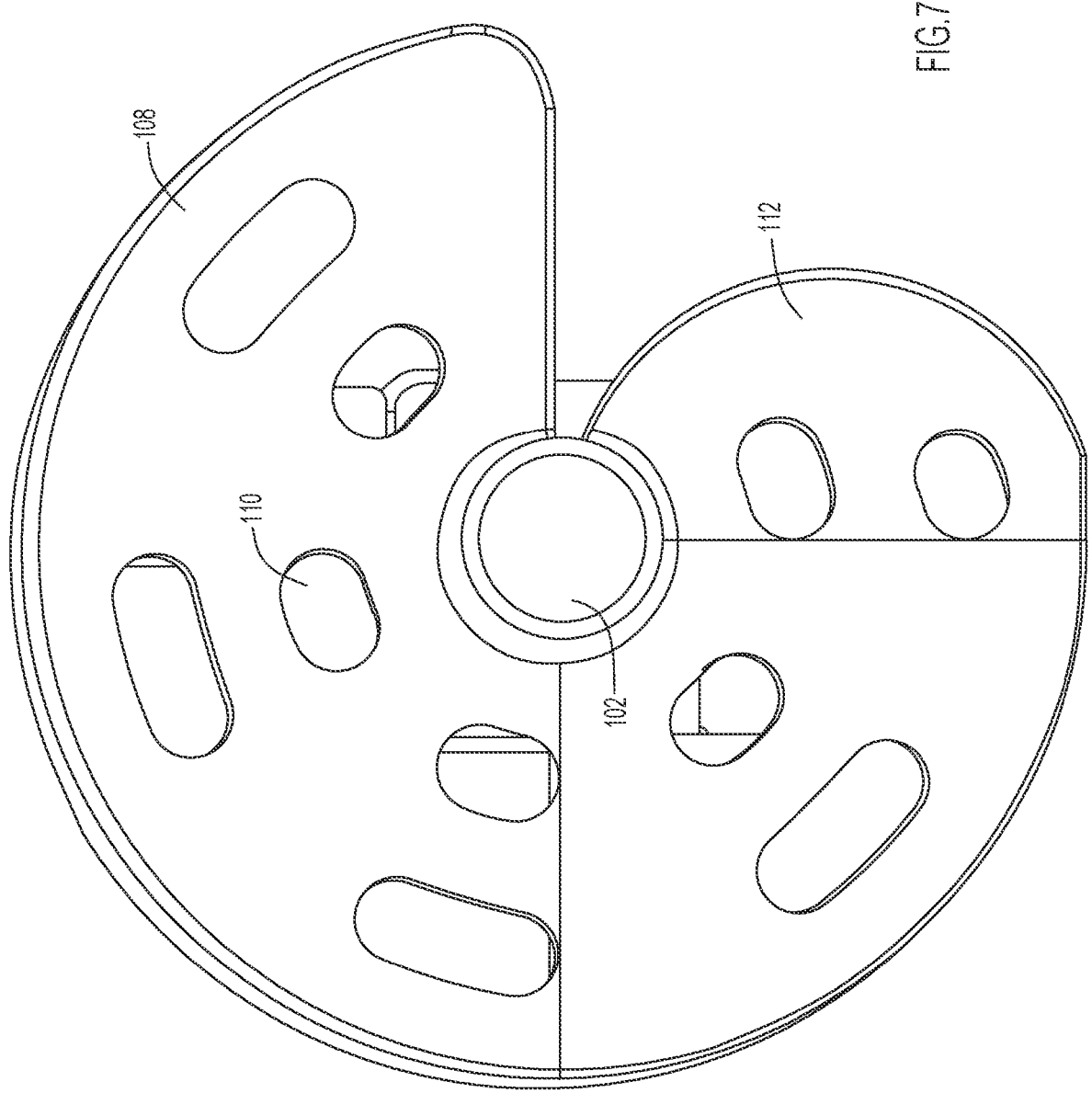
FIG. 7 shows a bottom view of an embodiment of the invention.

FIG. 7 shows a bottom view of an embodiment.

Figure 8:
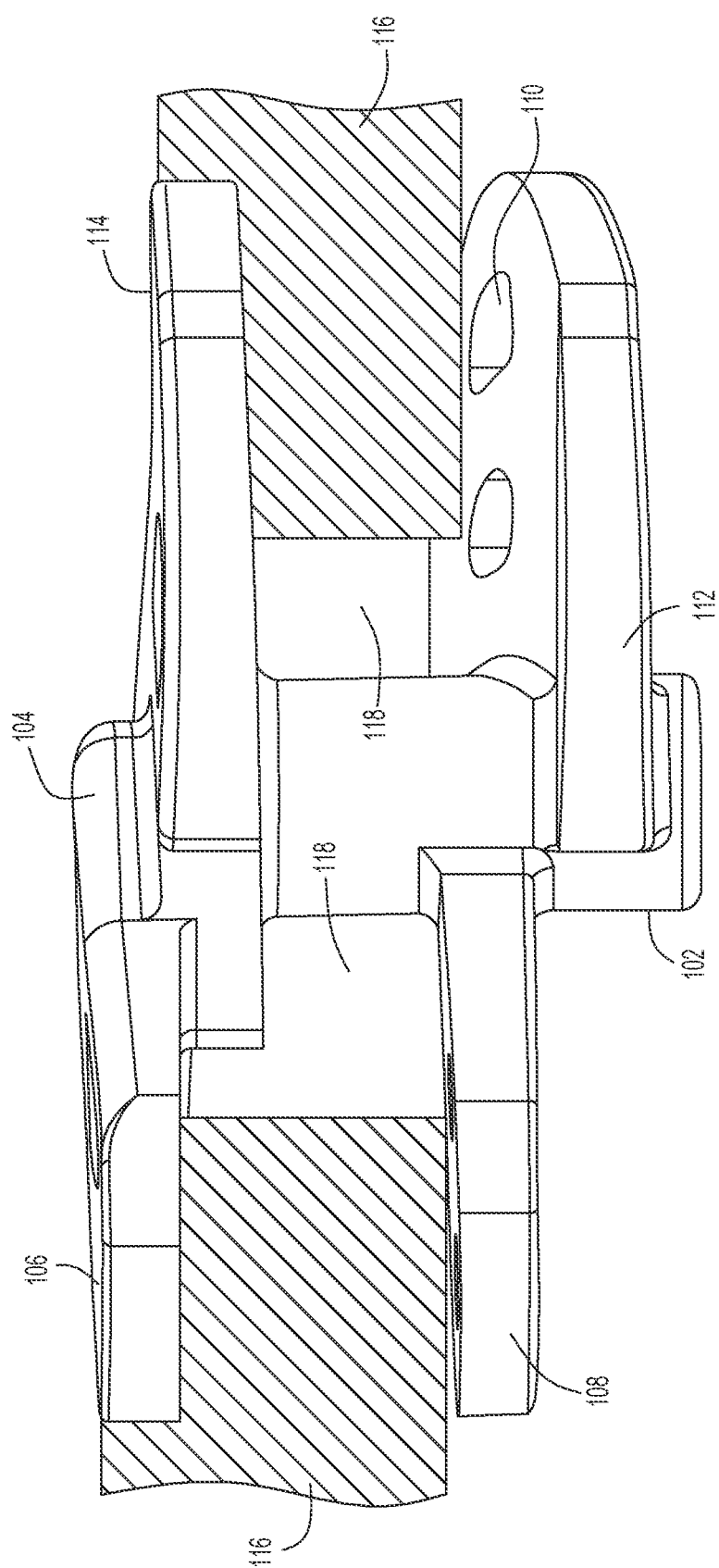
FIG. 8 shows a diagram of one or more embodiments of the device inserted into a wound.

FIG. 8 shows an embodiment of the device in place, inserted into the wound of the tissue 116. The device acts to hold the tissue in place around the wound 118 with minimal harm to the tissue. The central rod 102 may be between 20 and 95% of the width of the wound 118, with a range of 25-50% of the width of wound 118 expected to be more preferred. The width of the tissue scaffold is scaled to the wound width, with the plates extending over the edges of the wound such that at least 10% of the width of the upper and lower plate is seated against the upper and lower edge of wound 118, with an 11% to 25% radial overlap considered to provide greater stability and a 50% overlap providing maximal stability and chance for tissue ingrowth while still allowing the central rod to fit through the wound opening during insertion of the insertable tissue scaffold. The general width of the device will be matched to the size of the trocar used in the minimally invasive procedure. A device having a width of between 5 and 15 mm would be used on most defects. Scaffolds of variable sizes may be used to repair tissue defects of variable sizes. Larger diameter tissue scaffolds may be required to repair eccentric shaped abdominal defects. It is envisioned that in clinical use, the defect could be measured and the scaffold manufactured (e.g. by 3D printing) on demand proximate to an operating room to allow the tissue scaffold to be tailored to the defect being repaired. Alternatively, the tissue scaffold can be selected from a variety of manufactured sizes to accommodate defects of differing depth and widths. Given that trocars are in standard sizes, it is believed that standard sized tissue scaffolds could be utilized for the routine trocar defect sizes.

As illustrated in FIG. 8, in order to optimize tissue alignment and healing and to reduce the risk of hernia complications, the scaffold is designed to extend beyond the edges of the defect. This anchors the device and prevents extrusion of prolapse of the scaffold during the healing biodegradation period.

In one or more embodiments, the device is used as follows. An insertion device is detachably coupled from above the upper plate 114 by coupling with the upper plate perforations 110, using the engagement block 104 to provide stability. After the trocar has been removed from the abdominal wall entry site, the joined insertion device and attached scaffold are placed in the trocar port site and positioned such that the lower plate 108 engages the peritoneal layer of the intra-abdominal cavity and/or the fascia muscle layer within the length of the tissue tunnel. The helical shape contains a camber feature that services to draw or pull tissue around the wound defect into the scaffold during the course of deploying the scaffold. At that point in time, the insertion tool can be detached from the scaffold and removed from the operative field. The implantable scaffold has engaged tissue between the upper plate 106 and lower plate 108, securing tissue in anatomical alignment while the trocar port has time to heal. The upper plate perforations 110 and lower base perforations 110 are there to encourage the tissue ingrowth into the scaffold and facilitate healing of the trocar port defect.

As shown in the illustrated embodiments, the upper plate 106 and lower plate 108 have two quadrants that are essentially parallel to each other and are displaced from each other by a single plate thickness. A third quadrant is cambered to allow the upper and lower plates to have an essentially uniform thickness while one quadrant is one plate thickens further up or down the central rod 102. This is best shown visualized in FIG. 5. This cambered helical structure and curved edges of the plates provide a tactile feel fo the scaffold during implantation, aids in the proper seating of the device and provides useful haptic feedback and assurance that the tissue scaffold is securely engaged with the tissue.

General Composition of the Wound Closure Device

Materials specified for the wound closure device are specific for its intended application and use. The scope of materials that will satisfy the requirements of this application is unusually narrow. This is a direct consequence of the specificity and functional demands characteristic of the intended surgical application.

The intention for the wound closure device is to close and secure the trocar port defect in the fascia. This requires a known and finite healing interval of some three to five months. Its purpose fulfilled at the end of this period, making continued presence of the closure device a potential liability. Maurus and Kaeding (Maurus, P. B. and Kaeding, C. C., "Bioabsorbable Implant Material Review", *Oper. Tech. Sports Med* 12, 158-160, 2004) describe the advantages of a device that is biodegradable. This means that the materials will degrade or disintegrate, being absorbed in the surrounding local tissue environment after a definite, predictable, and desired period of time. One advantage of such materials over non-degradable or essentially stable materials is that after the interval for which they are applied (i.e. healing time) has elapsed, they are fully biodegraded and do not act as a residual foreign body. This is most significant as it minimizes risks associated with foreign body reaction, chronic inflammation and/or suture granuloma. Furthermore, the presence of the scaffold structure supports tension free anatomic alignment of the tissue defect and facilitates wound healing.

A disadvantage of these types of materials is that their biodegradable characteristic makes them susceptible to degradation under normal ambient conditions. There is usually sufficient moisture or humidity in the atmosphere to initiate their degradation even upon relatively brief exposure. This means that precautions must be taken throughout their processing and fabrication into useful forms, and in their storage and handling, to avoid moisture absorption. This is not a serious limitation as many materials require handling in controlled atmosphere chambers and sealed packaging; but it is essential that such precautions are observed. Middleton and Tipton (Middleton, J. and Tipton A. "Synthetic Biodegradable Polymers As Medical Devices" *Medical Plastics and Biomaterials Magazine*, March 1998) found that this characteristic also dictates that their sterilization before surgical use cannot be done using autoclaves, but alternative approaches must be employed (e.g. exposure to atmospheres of ethylene oxide or gamma radiation with cobalt 60).

While biodegradability is an essential material characteristic for the wound closure device, the intended application is such that a further requirement is that the material is formulated and manufactured with sufficient compositional and process control to provide a precisely predictable and reliable degree of biodegradability. The period of biodegradability corresponds to the healing interval for the trocar defect in the fascia layer, which is typically three to five months.

In these materials, simple chemical hydrolysis of the hydrolytically unstable backbone of the polymer is the prevailing mechanism for its degradation. As discussed in Middleton and Tipton (Middleton, J. and Tipton A referenced previously), this type of degradation when the rate at which water penetrates the material exceeds that at which the polymer is converted into water-soluble materials is known as bulk erosion.

Biodegradable polymers may be either natural or synthetic. In general, synthetic polymers offer more advantages than natural materials in that their compositions can be more readily finely-tuned to provide a wider range of properties and better lot-to-lot uniformity and, accordingly, offer more general reliability and predictability and are the preferred source.

Synthetic absorbable materials have been fabricated primarily from three polymers: polyglycolic acid (PGA), polylactic acid (PLA) and polydioxanone (PDS). These are alpha polyesters or poly (alpha-hydroxy) acids. The dominant ones are PLA and PGA and have been studied for several decades. Gilding and Reed (Gilding, D. K and Reed A. M., "Biodegradable Polymers for Use in Surgery" *Polymer* 20, 1459-1464) discussed how each of these materials has distinctive, unique properties. One of the key advantages of these polymers is that they facilitate the growth of blood vessels and cells in the polymer matrix as it degrades, so that the polymer is slowly replaced by living tissue as the polymer degrades.

In recent years, researchers have found it desirable for obtaining specific desirable properties to prepare blends of these two dominant types, resulting in a highly useful form, or co-polymer, designated as PLGA or poly (lactic-co-glycolic acid). Asete and Sabilov (Asete, C. E. and Sabilov C. M., "Synthesis and Characterization of PLGA Nanoparticles", *Journal of Biomaterials Science—Polymer Edition* 17 (3) 247-289 (2006)) discuss how this form is currently used in a host of FDA-approved therapeutic devices owing to its biodegradability and biocompatibility.

In one or more embodiments, the biodegradable wound closure device may be made of biodegradable material of different stability (i.e. half-life). While it is important for the material that is in direct contact with the fascia needs to stay in place for a few months, while the rest of the implantable structure can degrade significantly in a matter of weeks without affecting the performance of the payload. In one or more embodiments.

We claim:

1. An implantable tissue scaffold for closing a wound defect comprising:

one central rod having a central longitudinal axis;

an upper plate including an upper section, a lower section disposed below the upper section, and a middle section attached to the central rod and connecting the upper and lower sections, the upper, middle and lower sections collectively at least partially circumscribing the central rod, the middle section being a helical section that at least partially circumscribes the central rod, the upper plate having a first end and an opposite second end that is each connected to the central rod, each of the upper section and lower section being perpendicular to the longitudinal axis of the central rod, a lower end of the lower section being fixed to the central rod; and a lower plate spaced-apart from the upper plate, the lower plate including an upper section, a lower section disposed below the upper section of the lower plate, and a middle section attached to the central rod and connecting the upper and lower sections of the lower plate, the upper, middle and lower sections of the lower plate collectively at least partially circumscribing the central rod, the middle section of the lower plate being a helical section that at least partially circumscribes the central rod, the lower plate having a first end and an opposite second end that is each connected to the central rod, each of the upper section and lower section of the lower plate being perpendicular to the longitudinal axis of the central rod, a lower end of the lower section being fixed to the central rod;

the helical section of the upper plate and/or the helical section of the lower plate including a camber feature that is configured to draw tissue around the wound into the scaffold, the central rod, upper plate and lower plate comprising a single unitary piece made of a biodegradable material.

2. The implantable tissue scaffold according to claim 1, wherein the helical section of one or both of the lower plate and upper plate circumscribes the central rod by less than 360 degrees.

3. The implantable tissue scaffold according to claim 1, wherein the helical section of one or both of the lower plate and upper plate circumscribes the central rod by greater than 360 degrees.

4. The implantable tissue scaffold according to claim 1, wherein one or both of the upper plate and lower plate includes a geometry that promotes tissue ingrowth into the respective upper plate and lower plate.

5. The implantable tissue scaffold of claim 4, wherein the geometry that promotes tissue ingrowth includes a plurality of perforations.

6. The implantable tissue scaffold according to claim 5, wherein the plurality of perforations include through holes in the one or both of the upper plate and lower plate.

7. The implantable tissue scaffold according to claim 5, wherein the plurality of perforations include a first set of perforations and a second set of perorations, the first set of perforations being located radially nearer the central rod than the second set of perforations.

8. The implantable tissue scaffold according to claim 1, wherein one or both of the upper and lower plates includes a textured surface.

9. The implantable tissue scaffold according to claim 1, wherein the biodegradable material is configured to completely biodegrade in three to five months after being implanted into a laparoscopic port defect.

10. The implantable tissue scaffold according to claim 1, wherein the lower and upper plates comprise a same shape.

11. The implantable tissue scaffold according to claim 10, wherein the lower and upper plates are arranged about the central rod in a same way.

12. The implantable tissue scaffold according to claim 1, wherein the upper section of the upper plate includes a first flat surface that lies in a first plane that is perpendicular to the central longitudinal axis of the central rod and the upper section of the lower plate includes a second flat surface that lies in a second plane that is perpendicular to the central longitudinal axis of the central rod, the first flat surface and the second flat surface being parallel to one another and facing one another.

13. The implantable tissue scaffold according to claim 1, wherein the lower section of the upper plate includes a first flat surface that lies in a first plane that is perpendicular to the central longitudinal axis of the central rod and the lower section of the lower plate includes a second flat surface that lies in a second plane that is perpendicular to the central longitudinal axis of the central rod, the first flat surface and the second flat surface being parallel to one another and facing one another.

14. An implantable tissue scaffold for closure of a laparoscopic tissue defect comprising:

a tissue scaffold body scaled to a laparoscopic trocar port defect, the scaffold body including:

one central rod having a central longitudinal axis;

an upper plate including an upper section, a lower section disposed below the upper section, and a middle section attached to the central rod and connecting the upper and lower sections, the upper, middle and lower sections collectively at least partially circumscribing the central rod, the middle section being a helical section that at least partially circumscribes the central rod, the upper plate having a first end and an opposite second end that is each connected to the central rod, each of the upper section and lower section being perpendicular to the longitudinal axis of the central rod, a lower end of the lower section being fixed to the central rod; and a lower plate spaced-apart from the upper plate by a defect thickness dimension, the lower plate including an upper section, a lower section disposed below the upper section of the lower plate, and a middle section attached to the central rod and connecting the upper and lower sections of the lower plate, the upper, middle and lower sections of the lower plate collectively at least partially circumscribing the central rod, the middle section of the lower plate being a helical section that at least partially circumscribes the central rod, the lower plate having a first end and an opposite second end that is each connected to the central rod, each of the upper section and lower section of the lower plate being perpendicular to the longitudinal axis of the central rod, a lower end of the lower section being fixed to the central rod;

the helical section of the upper plate and/or the helical section of the lower plate including a camber feature that is configured to draw tissue around the laparoscopic tissue defect into the scaffold, the central rod, upper plate and lower plate comprising a single unitary piece made of a biodegradable material.

15. The implantable tissue scaffold according to claim 14, wherein the helical section of one or both of the lower plate and upper plate circumscribes the central rod by less than 360 degrees.

16. The implantable tissue scaffold according to claim 14, wherein one or both of the upper plate and lower plate includes a plurality of perforations that promote tissue ingrowth into the respective upper plate and lower plate.

17. The implantable tissue scaffold according to claim 16, wherein the plurality of perforations include through holes in the one or both of the upper plate and lower plate.

18. The implantable tissue scaffold according to claim 14, wherein the lower and upper plates comprise a same shape and a same size and are arranged about the central rod in a same way.

19. The implantable tissue scaffold according to claim 12, wherein the lower section of the upper plate includes a third flat surface that lies in a third plane that is perpendicular to the central longitudinal axis of the central rod and the lower section of the lower plate includes a fourth flat surface that lies in a fourth plane that is perpendicular to the central longitudinal axis of the central rod, the third flat surface and the fourth flat surface being parallel to one another and facing one another.

* * * * *

UNITED STATES PATENT AND TRADEMARK OFFICE
CERTIFICATE OF CORRECTION

| | |
|---|---|
| PATENT NO. | : 11,759,189 B2 |
| APPLICATION NO. | : 16/713005 |
| DATED | : September 19, 2023 |
| INVENTOR(S) | : Michael S. Klein |

It is certified that error appears in the above-identified patent and that said Letters Patent is hereby corrected as shown below:

In the Specification

Column 3, Line 43, change "laproscopic" to --laparoscopic--; and

Column 7, Line 6, change "fo" to --of--.

Signed and Sealed this
Thirteenth Day of February, 2024

*Katherine Kelly Vidal*

Katherine Kelly Vidal
*Director of the United States Patent and Trademark Office*